United States Patent [19]
Isozaki et al.

[11] Patent Number: 5,433,887
[45] Date of Patent: Jul. 18, 1995

[54] LIQUID CRYSTAL COMPOUNDS

[75] Inventors: Tadaaki Isozaki; Hiroyuki Mogamiya; Shigenori Sakuma; Noriko Yamakawa, all of Tokyo, Japan

[73] Assignee: Showa Shell Sekiyu Kabushiki Kaisha, Tokyo, Japan

[21] Appl. No.: 889,373

[22] Filed: May 28, 1992

Related U.S. Application Data

[63] Continuation-in-part of Ser. No. 736,593, Jul. 26, 1991, abandoned.

[30] Foreign Application Priority Data

Jul. 26, 1990 [JP] Japan ................... 2-198500

[51] Int. Cl.$^6$ .................. C09K 19/20; C07C 69/76
[52] U.S. Cl. ..................... 252/299.64; 252/299.67; 560/60; 560/73
[58] Field of Search .................. 252/299.01, 299.64, 252/299.67; 560/60, 73

[56] References Cited

U.S. PATENT DOCUMENTS

| | | | |
|---|---|---|---|
| 4,918,213 | 4/1990 | Nohira et al. | 252/299.65 |
| 4,921,632 | 5/1990 | Nakamura et al. | 252/299.67 |
| 5,184,847 | 2/1993 | Suzuki et al. | 252/299.67 |
| 5,204,020 | 4/1993 | Suzuki et al. | 252/299.67 |
| 5,207,946 | 5/1993 | Numazawa et al. | 252/299.67 |
| 5,207,947 | 5/1993 | Suzuki et al. | 252/299.67 |
| 5,211,879 | 5/1993 | Shiratori et al. | 252/299.67 |

FOREIGN PATENT DOCUMENTS 0350330  1/1990  European Pat. Off. .
2115145  4/1990  Japan .

OTHER PUBLICATIONS

Molecular Crystals and Liquid Crystals Incorporating Nonlinear Optics, vol. 174, Sep. 1989, pp. 89–99.
Patent Abstracts of Japan, vol. 13, No. 151 (C–584)[349], 12th Apr. 1989, p. 26 C 584.

*Primary Examiner*—Philip Tucker
*Attorney, Agent, or Firm*—Cushman Darby & Cushman

[57] ABSTRACT

The invention discloses optically active liquid crystal compounds represented by the formulas [I], [II] and [III]:

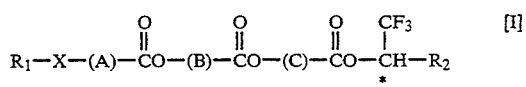

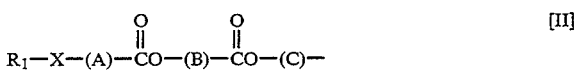

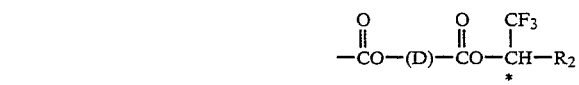

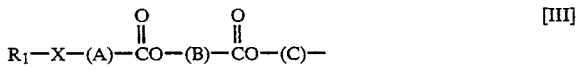

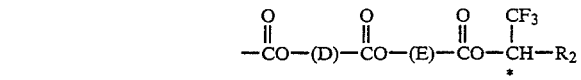

wherein $R_1$ and $R_2$ each represents an alkyl group of 4–18 carbon atoms, X represents O, COO or a single bond, and (A), (B), (C), (D) and (E) each represents

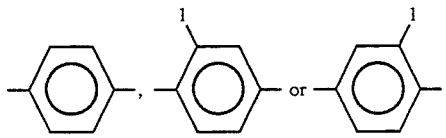

in which l represents a halogen.

The invention further discloses optically active liquid crystal compounds which are able to exhibit tristable states, represented by the formulas [IV], [V] and [VI]:

(Abstract continued on next page.)

-continued
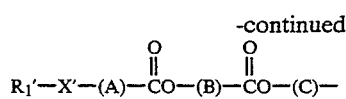  [V]
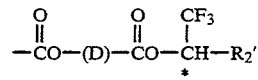
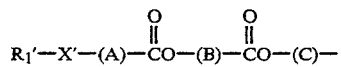  [VI]
-continued
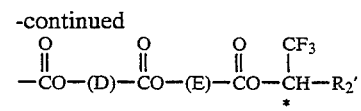
wherein $R_1'$ and $R_2'$ each represents a straight chain alkyl group of 5–16 carbon atoms, $X'$ represents O or COO and (A), (B), (C), (D) and (E), and l each has the same meaning as above.
6 Claims, 5 Drawing Sheets

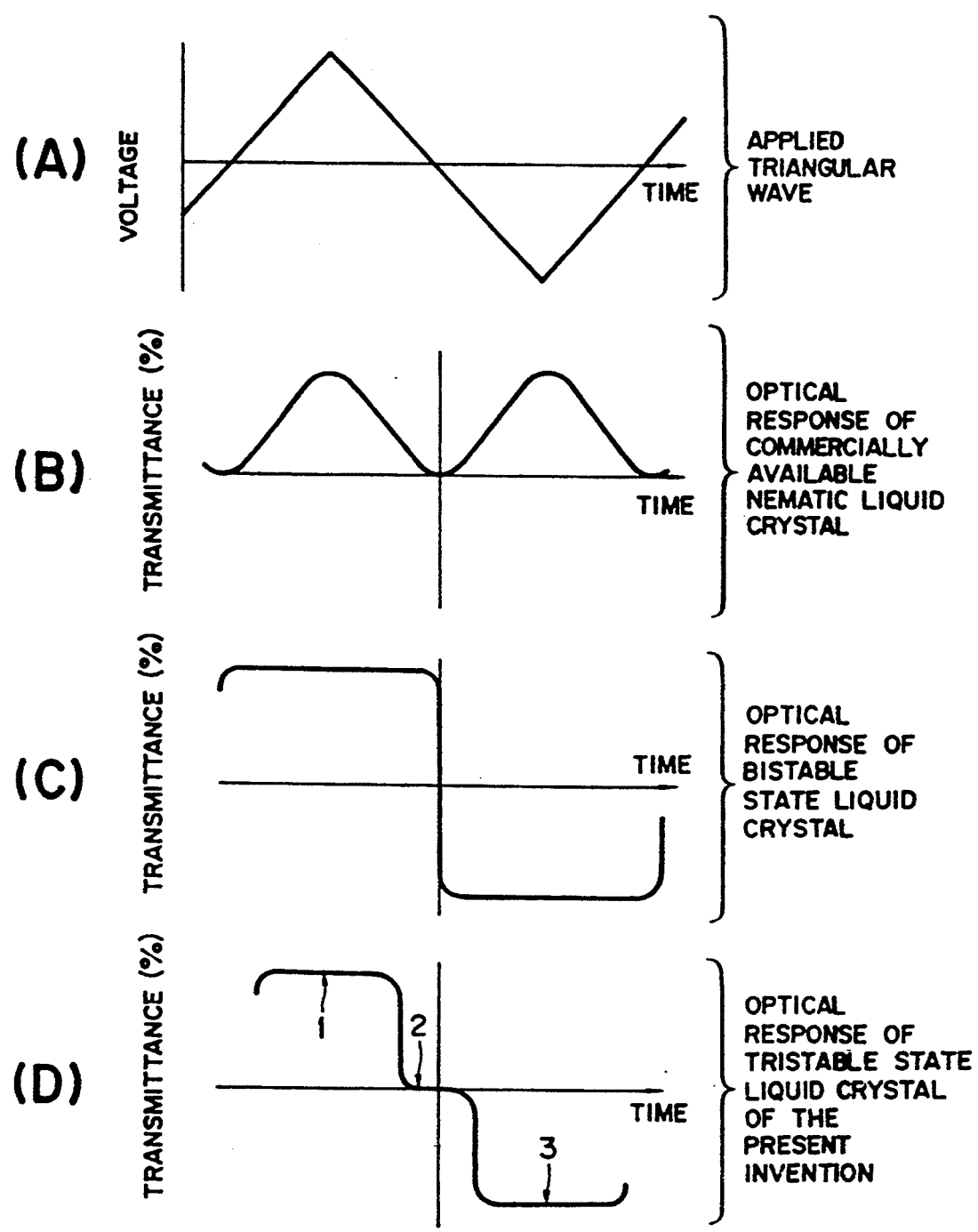

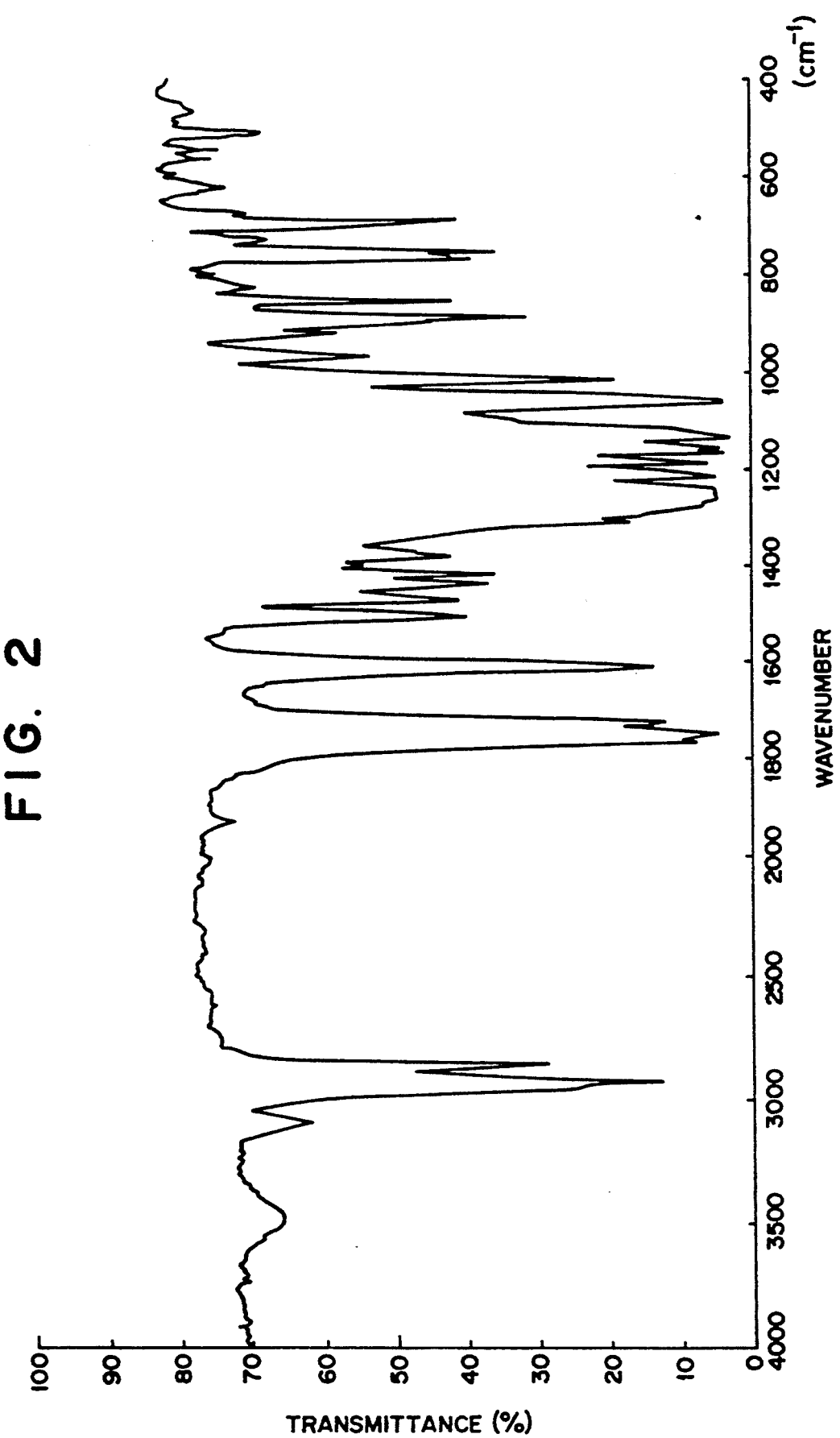

LIQUID CRYSTAL COMPOUNDS

This is a continuation-in-part of U.S. Ser. No. 07/736,593 filed on Jul. 26, 1991, now abandoned.

The present invention relates to liquid crystal compounds suitable to be used for electrooptical devices utilizing response of antiferroelectric liquid crystals to electric fields and in particular, to liquid crystal compounds which contain a phenylcarbonyloxy group and able to show optically tristable states.

Since liquid crystal display devices have excellent characteristics such as (1) low voltage operability, (2) low power consumption, (3) low thickness display, and (4) passive display device, TN type, STN type and Gest-Host type have been developed and put to practical use.

However, the display devices which are widely utilized in the market and use nematic liquid crystals are restricted because their response speed is as low as a few msec to some msec.

In order to solve these problems, STN type and active matrix type using a thin film transistor have been developed. Although the STN type display devices have been excellent in display qualities such as display contrast and viewing angle, there are problems that the control of cell gap or tilt angle requires a high accuracy and response is somewhat slow.

Therefore, development of novel liquid crystal display systems excellent in responsiveness has been demanded and it has been tried to develop ferroelectric liquid crystals which may make it possible to provide ultra-high speed devices having very short optical response time in the order of a few $\mu$sec.

As ferroelectric liquid crystals, DOBAMBC (p-decyloxybenzylidene-p-amino-2-methylbutyl cinnamate) is synthesized for the first time by Meyer et al. in 1975.

Further, ferroelectric liquid crystals such as DOBAMBC have attracted much attention because of their high speed response of submicro-second and memory characteristics in display devices as reported by Clark and Lagarwall in 1980. [N. A. Clark, et al., Appl. Phys. Lett., 36,899 (1980)].

However, their systems still have many technical tasks to be solved for practical use. Especially, there have been no compounds which are ferroelectric liquid crystals at room temperature and besides, there have not yet been established the methods which are effective and practical for control of liquid crystal molecular alignment which is essential for display.

Since the above report was made, many attempts have been made from both aspects of liquid crystal compounds and display devices utilizing the switching between twisted bistable states, but high contrast and proper threshold properties have not yet been obtained.

From these viewpoints, other switching systems have also been investigated and transitional scattering systems have been proposed. Thereafter, in 1988, a tristable state switching system of liquid crystals having tristable state reported [A. D. L. Chandani, T. Hagiwara, Y. Suzuki et al., Japan. J. of Appl. Phys., 27, (5), L729-L732 (1988)].

The term "tristable states" means that, in an electrooptical device where antiferroelectric liquid crystals are laid between the first electrode substrate plate and the second electrode substrate plate which is apart at a given space from the first one and it is constructed so that an electric voltage for electric field is applied to both the first and second electrode substrate plates, when voltage in the form of a triangular wave as shown in FIG. 1A is applied, the antiferroelectric liquid crystals have the first optically stable state (as shown as 2 in FIG. 1D) where no electric field is applied to, but upon application of electric field, the second optically stable state (as shown as 1 in FIG. 1D) which is different from the first stable state in one of electric field directions and the third optical stable state (as shown as 3 in FIG. 1D) which is different from the first and second stable states in the other direction of electric field, as shown in FIG. 1D.

The tristable state switching system employs clear threshold specificity and hysteresis to driving voltage exhibited by liquid crystal phase S*(3) having tristable states fundamentally different from the conventional bistable states in molecular orientation of liquid crystals. This is considered to be an epoch-making method by which a moving image of large scale can be displayed by simple matrix system. (Japanese Patent Kokai No. Hei 2-153322).

Liquid crystal compounds which are able to exhibit tristable states when they are in phase S*(3) are disclosed in Japanese Patent Kokai Nos. Hei 1-316339, 1-316367, 1-316372, 2-28128 and 1-213390.

As a result of intensive research conducted by the inventors on ester type liquid crystal compounds in view of the above-mentioned problems, it has been found that liquid crystal compounds containing a phenylcarbonyloxy group are chemically and photochemically stable and have large dielectric anisotropy and besides, have the liquid crystal phase S*( 3 ) having tristable states, which has not been obtained in the conventional ferroelectric liquid crystals.

That is, an object of the present invention is to provide novel liquid crystal compounds having phenyl ester groups, which are expected to be applicable to new electrooptical devices and liquid crystal display which utilize the liquid crystal phase S*(3) having optically tristable states.

BRIEF DESCRIPTION OF THE DRAWINGS

FIG. 1A shows triangular wave voltage applied, and FIGS. 1B, 1C and 1D show optical responses of commercially available nematic liqiud crystals, bistable state liquid crystals, and the present tristable state liquid crystals, repsectively.

FIG. 2 shows infrared absorption spectrum of the compound of the present invention obtained in Example 2.

Figure 3:
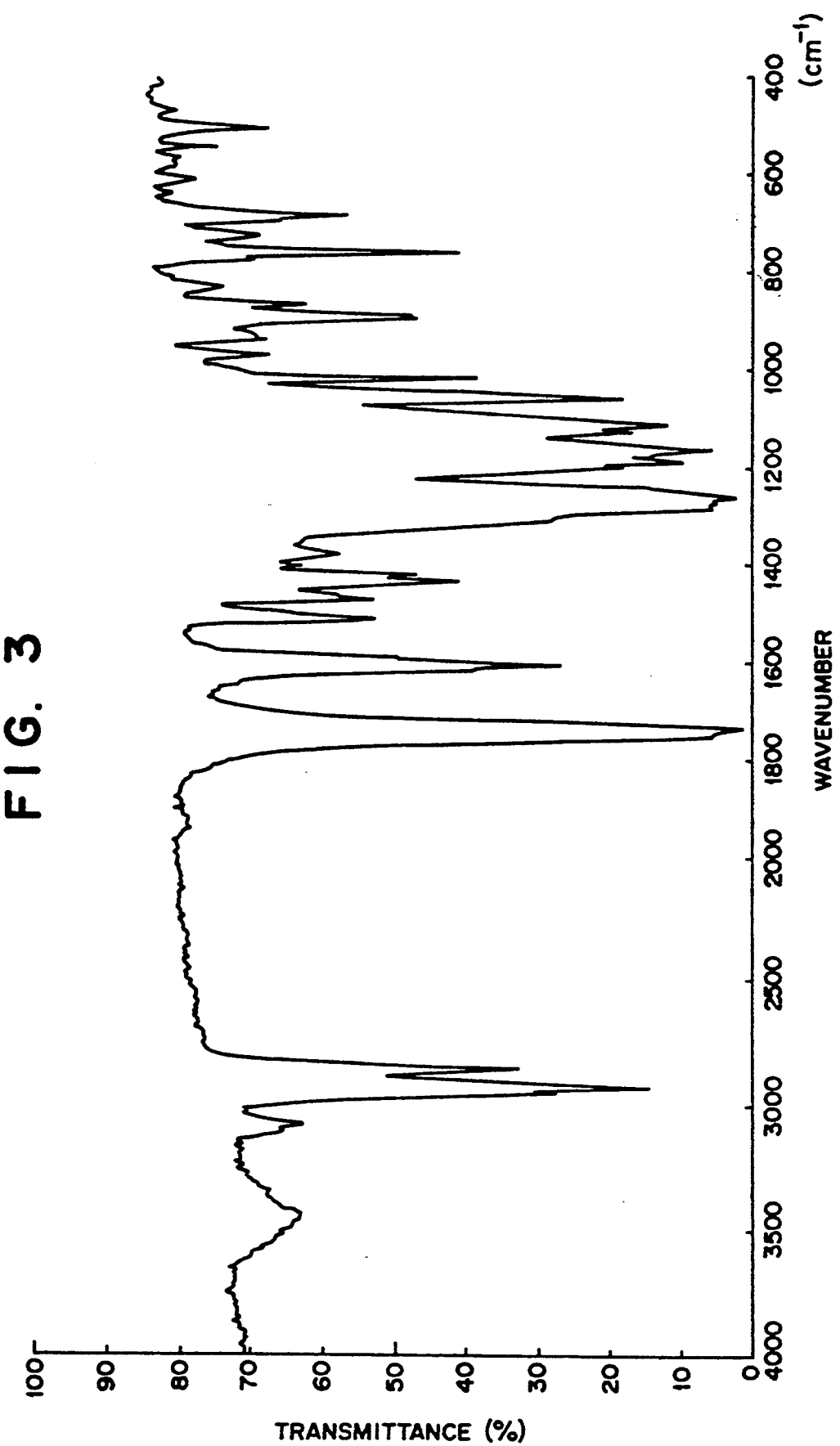
FIG. 3 shows infrared absorption spectrum of the compound of the present invention obtained in Example 3.

The first of the present invention relates to an optically active liquid crystal compound represented by the formula [I]:

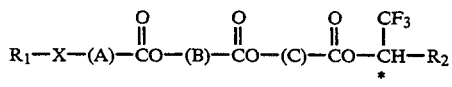

wherein $R_1$ and $R_2$ each represents an alkyl group of 4–18 carbon atoms, X represents O, COO or a single bond, and (A), (B) and (C) each represents

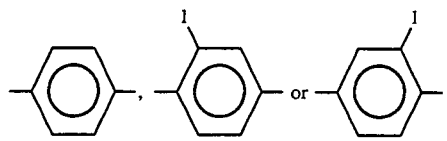

in which l represents a halogen atom.

The second of the present invention relates to an optically active liquid crystal compound represented by the formula [II]:

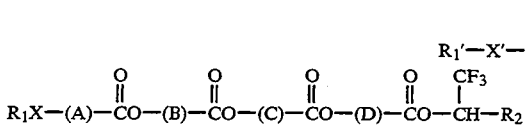

wherein $R_1$, $R_2$ and X each has the same meaning as above and (A), (B), (C) and (D) each represents

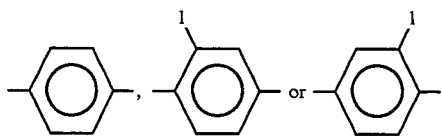

in which l represents a halogen atom.

The third of the present invention relates to an optically active liquid crystal compound represented by the formula [III]:

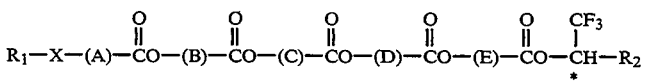

wherein $R_1$, $R_2$ and X each has the same meaning as above and (A), (B), (C), (D) and (E) each represents

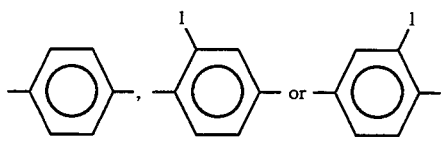

in which l represents a halogen atom.

The fourth of the present invention relates to an optically active liquid crystal compound having optically tristable states represented by the formula [IV]:

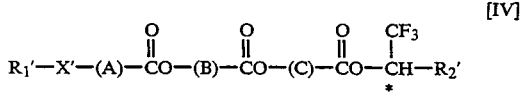

wherein $R_1'$ and $R_2'$ each represents a straight chain alkyl group of 5–16 carbon atoms, X' represents O or COO and (A), (B), (C) and l each has the same meaning as above.

The fifth of the present invention relates to an optically active liquid crystal compound having optically tristable states represented by the formula [V]:

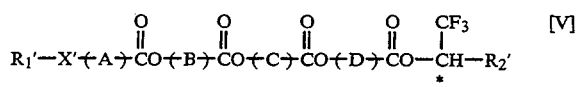

wherein $R_1'$, $R_2'$, X', (A), (B), (C), (D) and l each has the same meaning as above.

The sixth of the present invention relates to an optically active liquid crystal compound having optically tristable states represented by the formula [VI]:

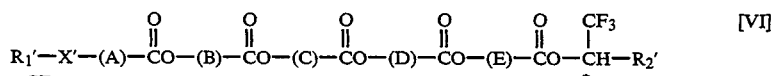

wherein $R_1'$, $R_2'$, X', (A), (B), (C), (D), (E) and l each has the same meaning as above and $R_1'$ and $R_2'$ each is preferably a straight chain alkyl group of 6–12 carbon atoms and l is preferably F or Cl.

One example of processes for preparing the compounds is shown below.

(1) A fatty acid chloride is allowed to react with p-hydroxybenzoic acid in the presence of triethylamine to obtain a 4-alkylcarbonyloxybenzoic acid, which is then converted to a 4-alkylcarbonyloxybenzoic acid chloride with excess thionyl chloride. This chloride is allowed to react with p-hydroxybenzoic acid in the presence of triethylamine to obtain a 4-(4-alkylcarbonyloxyphenylcarbonyloxy)benzoic acid, which is then converted to a 4-(4-alkylcarbonyloxyphenylcarbonyloxy)benzoic acid chloride with excess thionyl chloride.

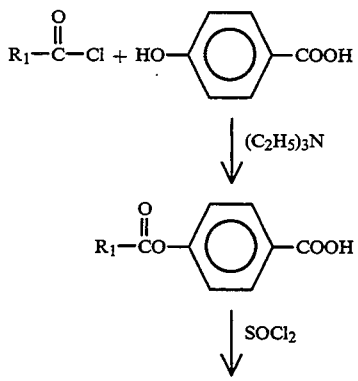

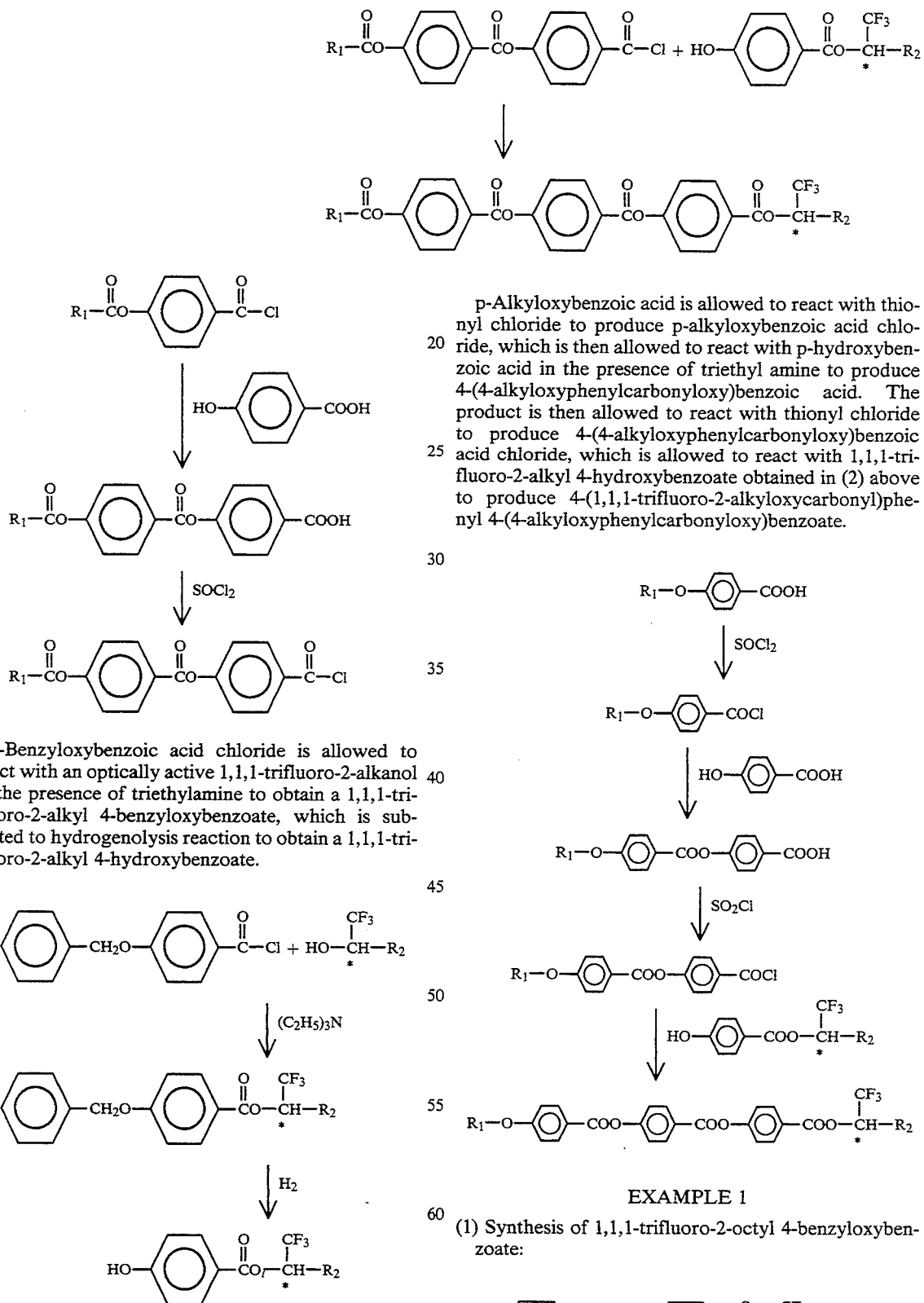

(2) 4-Benzyloxybenzoic acid chloride is allowed to react with an optically active 1,1,1-trifluoro-2-alkanol in the presence of triethylamine to obtain a 1,1,1-trifluoro-2-alkyl 4-benzyloxybenzoate, which is subjected to hydrogenolysis reaction to obtain a 1,1,1-trifluoro-2-alkyl 4-hydroxybenzoate.

(3) The chloride obtained in (1) is allowed to react with the phenol obtained in (2) in the presence of triethylamine to obtain a 4-(1,1,1-trifluoro-2-alkyloxycarbonyl)phenyl 4-[(4-alkylcarbonyloxy)phenylcarbonyloxy]benzoate.

p-Alkyloxybenzoic acid is allowed to react with thionyl chloride to produce p-alkyloxybenzoic acid chloride, which is then allowed to react with p-hydroxybenzoic acid in the presence of triethyl amine to produce 4-(4-alkyloxyphenylcarbonyloxy)benzoic acid. The product is then allowed to react with thionyl chloride to produce 4-(4-alkyloxyphenylcarbonyloxy)benzoic acid chloride, which is allowed to react with 1,1,1-trifluoro-2-alkyl 4-hydroxybenzoate obtained in (2) above to produce 4-(1,1,1-trifluoro-2-alkyloxycarbonyl)phenyl 4-(4-alkyloxyphenylcarbonyloxy)benzoate.

EXAMPLE 1

(1) Synthesis of 1,1,1-trifluoro-2-octyl 4-benzyloxybenzoate:

To a solution of 4-benzyloxybenzoic acid chloride (4.3 g) in methylene chloride (50 ml) was gradually added under ice cooling a solution of optically active 1,1,1-trifluoro-2-octanol (2.9 g), dimethylaminopyridine (0.6 g) and triethylamine (1.7 g) in methylene chloride (50 ml).

After the reaction mixture was left to stand to reach room temperature, reaction was allowed to proceed for 24 hours. The reaction mixture was poured in ice water and was extracted with methylene chloride. The methylene chloride layer was washed with dilute hydrochloric acid, water, 1N aqueous sodium carbonate solution, and water in this order and was dried over anhydrous magnesium sulfate. The solvent was distilled off to obtain a crude product. The product was subjected to toluene-silica gel column chromatography and was further recrystallized from ethanol to obtain the titled compound (3.8 g).

(2) Synthesis of 1,1,1-trifluoro-2-octyl 4-hydroxybenzoate:

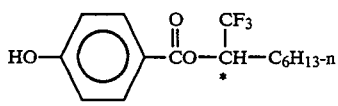

To a solution of the compound obtained in (1) above in methanol (100 ml) was added 10% Pd carried on carbon (0.4 g) and the mixture was subjected to hydrogenolysis reaction in a hydrogen atmosphere to obtain the titled compound (2.8 g).

(3) Synthesis of 4-n-decanoyloxybenzoic acid:

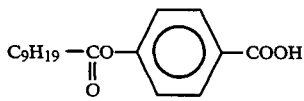

To a solution of p-hydroxybenzoic acid (3 g) and triethylamine (2.4 g) in dichloromethane (30 ml) were added decanoyl chloride (4.3 g) and dimethylaminopyridine (0.2 g) and the mixture was stirred for about 20 hours at room temperature. After dilute hydrochloric acid was added to the mixture, the organic layer was separated by a separating funnel. The solvent was distilled off and the residue was washed with n-hexane and then dried to obtain the titled compound (about 5 g).

(4) Synthesis of 4-n-decanoyloxybenzoic acid chloride:

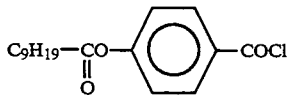

4-n-Decanoyloxybenzoic acid (5.0 g) obtained in (3) above was added to thionyl chloride (10 g) and a slight amount of N,N-dimethylformamide was added thereto, followed by refluxing for 4 hours. Unaltered thionyl chloride was distilled off to obtain the titled compound (5.2 g).

(5) Synthesis of 4-carboxyphenyl 4-n-decanoyloxybenzoate:

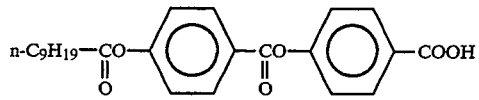

To a solution of p-hydroxybenzoic acid (2 g) and triethylamine (1.3 g) in methylene chloride (30 ml) were added 4-n-decanoyloxybenzoic acid chloride (4 g) obtained in (4) above and dimethylaminopyridine (0.3 g). The mixture was stirred at room temperature for about 20 hours. After dilute hydrochloric acid was added thereto, the organic layer was separated by a separating funnel. The solvent was distilled off and the residue was washed with n-hexane and then dried to obtain the titled compound (about 3 g).

(6) Synthesis of 4-(4-n-decanoyloxyphenylcarbonyloxy)benzoic acid chloride:

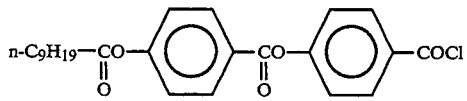

4-Carboxyphenyl 4-n-decanoyloxybenzoate obtained in (5) above (3 g) was added to thionyl chloride (about 10 g) and a very small amount of N,N-dimethylformamide was added thereto, followed by refluxing for 4 hours. Unaltered thionyl chloride was distilled off to obtain the titled compound (about 3.1 g).

(7) Synthesis of 4-(1,1,1-trifluoro-2-octyloxycarbonyl)phenyl 4-(4-n-decanoyloxyphenylcarbonyloxy)benzoate

To a solution of 1,1,1-trifluoro-2-octyl 4-hydroxybenzoate obtained in (2) above (0.5 g) and triethylamine (0.16 g) in methylenechloride (30 ml) was gradually added dropwise a solution of 4-(4-n-decanoyloxyphenylcarbonyloxy)benzoic acid chloride obtainer in (6) above (0.7 g) in methylene chloride (30 ml). Furthermore, dimethylaminopyridine (0.05 g) was added thereto and the mixture was stirred at room temperature for 24 hours. The reaction mixture was poured in water and the solution was made neutral. Then, the methylene chloride layer was separated and dried over anhydrous magnesium sulfate. Then, methylene chloride was distilled off. The residue was purified by silica gel column chromatography (developer: hexane/ethyl acetate=20/1) to obtain the titled compound (0.11 g).

Specific rotation $[\alpha]_D^{20} = +25.5°$

Phase transition temperatures (°C.) which were observed under a polarizing microscope using a hot stage were

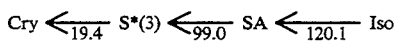

where S*(3): Optically tristable state liquid crystal phase

EXAMPLE 2

(1) Synthesis of 1,1,1-trifluoro-2-octyl 2-fluoro-4-benzyloxybenzoate:

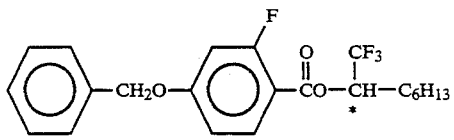

To a solution of 2-fluoro-4-benzyloxybenzoic acid chloride (2.7 g) in methylene chloride (30 ml) was gradually added under ice cooling a solution of optically active 1,1,1-trifluoro-2-octanol (1.8 g), dimethylaminopyridine (0.3 g) and triethylamine (1.5 g) in methylene chloride (50 ml).

After the reaction mixture was left to stand to reach room temperature, a reaction was allowed to proceed for 24 hours. The reaction mixture was poured in ice water and was extracted with methylene chloride. The extracted methylene chloride layer was washed with dilute hydrochloric acid, water, 1N aqueous sodium carbonate solution, and water in this order and was dried over anhydrous magnesium sulfate. The solvent was distilled off to obtain a crude product. The product was subjected to toluene-silica gel column chromatography and was further recrystallized from ethanol to obtain the titled compound (2.5 g).

(2) Synthesis of 1,1,1-trifluoro-2-octyl 2-fluoro-4-hydroxybenzoate:

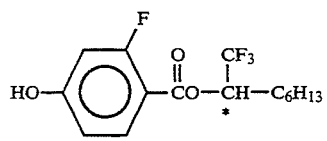

To a solution of the compound obtained in (1) above in methanol (100 ml) was added 10% Pd carried on carbon (0.25 g) and the mixture was subjected to hydrogenolysis reaction in a hydrogen atmosphere to obtain the titled compound (1.8 g).

(3) Synthesis of 3-fluoro-4-(1,1,1-trifluoro-2-octyloxycarbonyl)phenyl 4-(4-n-decanoyloxyphenylcarbonyloxy)benzoate

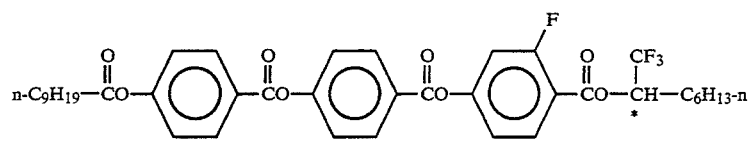

To a solution of 1,1,1-trifluoro-2-octyl 2-fluoro-4-hydroxybenzoate obtained in (2) above (0.5 g) and triethylamine (0.16 g) in methylenechloride (30 ml) was gradually added dropwise a solution of 4-(4-n-decanoyloxyphenylcarbonyloxy) benzoic acid chloride obtained in (6) of Example 1 (0.7 g) in methylene chloride (30 ml). Furthermore, dimethylaminopyridine (0.05 g) was added thereto and the mixture was stirred at room temperature for 24 hours. The reaction mixture was poured in water and the solution was made neutral. Then, the methylene chloride layer was separated and dried over anhydrous magnesium sulfate. Then, methylene chloride was distilled off. The residue was purified by silica gel column chromatography (developer: hexane/ethyl acetate=20/1) to obtain the titled compound (0.13 g).

Specific rotation $[\alpha]_D^{20} = +23.8°$

Phase transition temperatures (°C.) which were observed under a polarizing microscope using a hot stage were

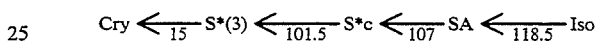

where S* (3): optically tristable state liquid crystal phase

IR spectrum of the titled compound is shown in FIG. 2.

EXAMPLE 3

Synthesis of 4-(1,1,1-trifluoro-2-octyloxycarbonyl)phenyl 2-fluoro-4-(4-n-decanoyloxyphenylcarbonyloxy)benzoate:

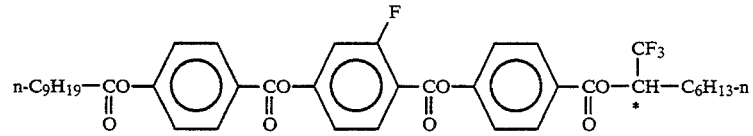

Example 1 was repeated except that 2-fluoro-4-hydroxybenzoic acid (2 g) was used in place of the p-hydroxybenzoic acid used in (5) of Example 1 to obtain the titled compound (0.08 g).

Phase transition temperatures (°C.) which were observed under a polarization microscope using a hot stage were

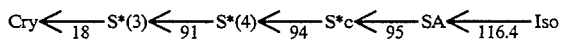

wherein S*(3): opticaly tristable state liquid crystal phase

S*(4): optically tetrastable state liquid crystal phase

IR spectrum of the titled compound is shown in FIG. 3.

EXAMPLE 4

Synthesis of 3-fluoro-4-(1,1,1-trifluoro-2-octyloxycarbonyl)phenyl 2-fluoro-4-(4-n-decanoyloxyphenylcarbonyloxy)benzoate:

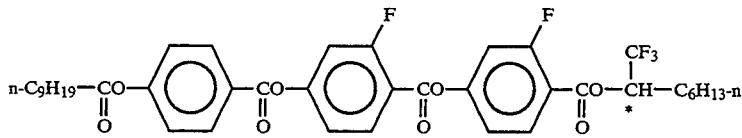

Example 1 was repeated except that 2-fluoro-4-hydroxybenzoic acid (2 g) was used in place of the p-hydroxybenzoic acid used in (5) of Example 1 and 2-fluoro-4-benzyloxybenzoic acid chloride (4.3 g) was used in place of the 4-benzyloxybenzoic acid chloride used in (1) of Example 1 to obtain the titled compound (0.02 g).

Phase transition temperatures (°C.) which were observed under a polarization microscope using a hot stage were $$Cry \underset{-25}{\longleftrightarrow} Sx \underset{-5}{\longleftrightarrow} S^*(3) \underset{97}{\longleftrightarrow} S^*c \underset{103}{\longleftrightarrow} SA \underset{115.8}{\longleftrightarrow} Iso$$

where S*(3): optically tristable state liquid crystal phase
Sx: A liquid crystal phase having field response, which has higher numbers of stable state.

The novel liquid crystal compounds of the present invention all have tristable states and have a wide variety of applications such as display devices and switching devices.

EXAMPLE 5

(1) Synthesis of 4-n-octyloxybenzoic acid chloride:

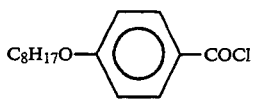

4-n-Octyloxybenzoic acid (4.3 g) was added to thionyl chloride (10 g) and a slight amount of N,N-dimethylformamide was added thereto, followed by refluxing for 4 hours. Unaltered thionyl chloride was distilled off to obtain the titled compound (4.5 g).

(2) Synthesis of 4-carboxyphenyl 4-n-octylbenzoate:

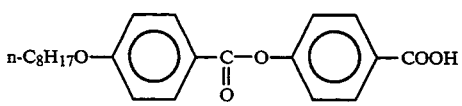

To a solution of p-hydroxybenzoic acid (2 g) and triethylamine (1.3 g) in methylene chloride (30 ml) were added 4-n-octyloxybenzoic acid chloride (3.4 g) obtained in (1) and dimethylaminopyridine (0.3 g). The mixture was stirred at room temperature for about 20 hours. After dilute hydrochloric acid was added thereto, the organic layer was separated by a separating funnel. The solvent was distilled off and the residue was washed with n-hexane and then dried to obtain the titled compound (about 2.7 g).

(3) Synthesis of 4-(4-n-octyloxyphenylcarbonyloxy)benzoic acid chloride:

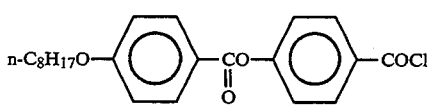

4-Carboxyphenyl 4-n-octyloxybenzoate obtained in (2) above (2.7 g) was added to thionyl chloride (about 10 g) and a very small amount of N,N-dimethylformamide was added thereto, followed by refluxing for 4 hours. Unaltered thionyl chloride was distilled off to obtain the titled compound (about 3.1 g).

(4) Synthesis of 4-(1,1,1-trifluoro-2-octyloxycarbonyl)phenyl 4-(4-n-octyloxyphenylcarbonyloxy)benzoate

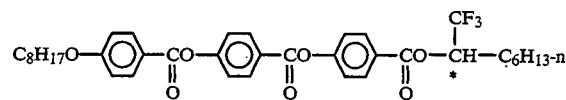

To a solution of 1,1,1-trifluoro-2-octyl 4-hydroxybenzoate obtained in (2) of example 1 above (0.5 g) and triethylamine (0.16 g) in methylenechloride (30 ml) was gradually added dropwise a solution of 4-(4-n-octyloxyphenylcarbonyloxy)benzoic acid chloride obtained in (3) above (0.6 g) in methylene chloride (30 ml). Furthermore, dimethylaminopyridine (0.05 g) was added thereto and the mixture was stirred at room temperature for 24 hours. The reaction mixture was poured in water and the solution was made neutral. Then, the methylene chloride layer was separated and dried over anhydrous magnesium sulfate. Then, methylene chloride was distilled off. The residue was purified by silica gel column chromatography (developer: hexane/ethyl acetate=20/1) to obtain the titled compound (0.10 g).

Specific rotation $[\alpha]_D^{20} = +25.5°$

Phase transition temperatures (°C.) which were observed under a polarization microscope using a hot stage were $$Cry \underset{61.2}{\overset{83.6}{\rightleftarrows}} S^*(3) \underset{99.0}{\overset{100.3}{\rightleftarrows}} SA \underset{123.2}{\overset{121.9}{\rightleftarrows}} Iso$$

where S*(3): optically tristable state liquid crystal phase.

EXAMPLE 6

Synthesis of 4-(1,1,1-trifluoro-2-decyloxycarbonyl)phenyl (R)-(+)-4-(4-n-octylbenzoyloxy)benzoyloxybenzoate:

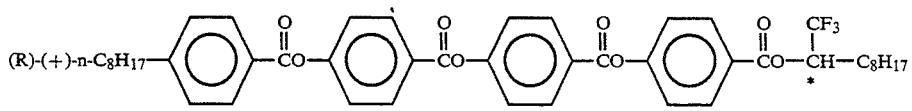

(1) Synthesis of p-octylbenzoic acid chloride:

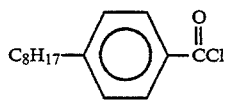

To a solution of p-octylbenzoic acid (4.7 g) in thionyl chloride (10 g) was added a small amount of N,N-dimethylformamide. The solution was heated under refluxing for 4 hours. Unaltered thionyl chloride was distilled off to obtain the titled compound (4.9 g).

(2) Synthesis of 4-(4-octylphenylcarbonyloxy)benzoic acid:

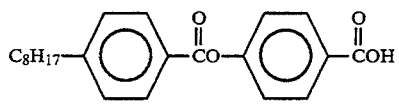

To a solution of p-hydroxybenzoic acid (2.4 g) and triethylamine (1.9 g) in dichloromethane (30 ml) were added p-octylbenzoic acid chloride (4.9 g) prepared in (1) above and dimethylaminopyridine (0.6 g). The solution was stirred at a room temperature for about 20 hours. After dilute hydrochloric acid solution was added, separation of the organic layer was made with a separating funnel. After the solvent was distilled off, the residue was washed with n-hexane and dried to obtain the titled compound (about 5 g).

(3) Synthesis of 4-(4-octylphenylcarbonyloxy)benzoic acid chloride:

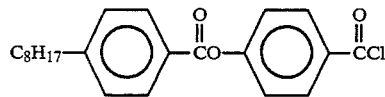

To a solution of 4-(4-octylphenylcarbonyloxy)benzoic acid (4.9 g) prepared in (2) above in thionyl chloride (10 g) was added a small amount of N,N-dimethylformamide. The solution was heated under refluxing for 4 hours. Unaltered thionyl chloride was distilled off to obtain the titled compound (5.0 g).

(4) Synthesis of 4-[4-(4-octylphenylcarbonyloxy)-phenylcarbonyloxy]benzoic acid:

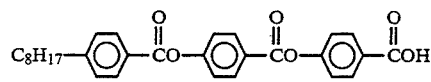

To a solution of p-hydroxybenzoic acid (1.6 g) and triethylamine (1.3 g) in dichloromethane (50 ml) were added 4-(4-octylphenylcarbonyloxy)benzoic acid chloride (5.0 g) prepared in (3) above and dimethylaminopyridine (0.5 g). The solution was stirred at a room temperature for about 30 hours. After dilute hydrochloric acid solution was added, the organic layer was separated with a separating funnel. After the layer was distilled to remove the solvent, the residue was washed with n-hexane and dried to obtain the titled compound (about 3 g).

(5) Synthesis of 4-[4-(4-octylphenylcarbonyloxy)-phenylcarbonyloxy]benzoic acid chloride:

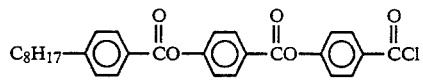

To a solution of 4-[4-(4-octylphenylcarbonyloxy)-phenylcarbonyloxy]benzoic acid (3 g) prepared in (4) in thionyl chloride (10 g) was added a small amount of N,N-dimethylformamide. The solution was heated under refluxing for 4 hours. Distillation was applied to remove unaltered thionyl chloride until the titled compound (3.1 g) was obtained.

(6) Synthesis of (R)-(+)-1,1,1-trifluoro-2-decyl 4benzyloxybenzoate:

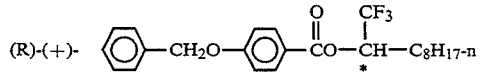

To a solution of 4-benzyloxybenzoic acid chloride (4.3 g) in methylene chloride (50 ml) was added drop by drop under ice cooling a solution of optically active (R)-(+)-1,1,1-trifluoro-2-decanol (3.3 g), dimethylaminopyridine (0.6 g) and triethylamine (1.7 g) in methylene chloride (50 ml). After the temperature of the solution went to the room temperature, the solution was left to stand for 24 hours. The solution was poured in ice water and extracted with methylene chloride. The methylene chloride layer was washed with a dilute hydrochloric acid solution, water, 1N aqueous sodium carbonate solution and water successively in this order before being dried over anhydrous magnesium sulfate. Distillation of the dried layer to remove the solvent gave a crude product of the titled compound. After the product was purified by toluene-silica gel column chromatography, recrystallization from ethanol gave the titled compound (4.1 g).

(7) Synthesis of (R)-(+)-1,1,1-trifluoro-2-decyl 4hydroxybenzoate:

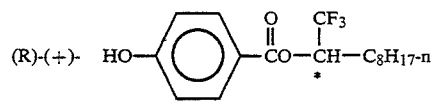

To a solution of the compound obtained in (6) above in methanol (100 ml) was added 10% Pd on carbon (0.4 g). The solution was subjected to hydrocracking in a hydrogen atmosphere to obtain the titled compound (3.1 g).

(8) Synthesis of (R)-(+)-4-(1,1,1-trifluoro-2-octyloxycarbonyl)phenyl 4-[4-(4-octylphenylcarbonyloxy) phenylcarbonyloxy]benzoate:

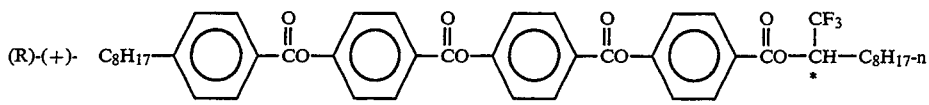

To a solution of 1,1,1-trifluoro-2-decyl 4-hydroxybenzoate (1.0 g) prepared in (7) above and triethylamine (0.35 g) in methylene chloride (50 ml) was added drop by drop a solution of 4-[4-(4-octylphenylcarbonyloxy)phenylcarbonyloxy]benzoic acid chloride (1.8 g) prepared in (5) above in methylene chloride (50 ml), before dimethylaminopyridine (0.12 g) was added. The solution was stirred at a room temperature for 24 hours, before being poured in water and controlled to neutral. After the methylene chloride layer was separated, the layer was dried over anhydrous magnesium sulfate before being distilled to remove the methylene chloride. The residue was purified by silica gel column chromatography (developer: hexane/ethyl acetete=20/1) to obtain the titled compound (0.12 g).

Phase transition temperatures under a polarizing microscope using a hot stage were as follows;

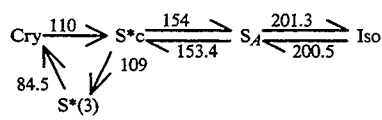

Figure 4:
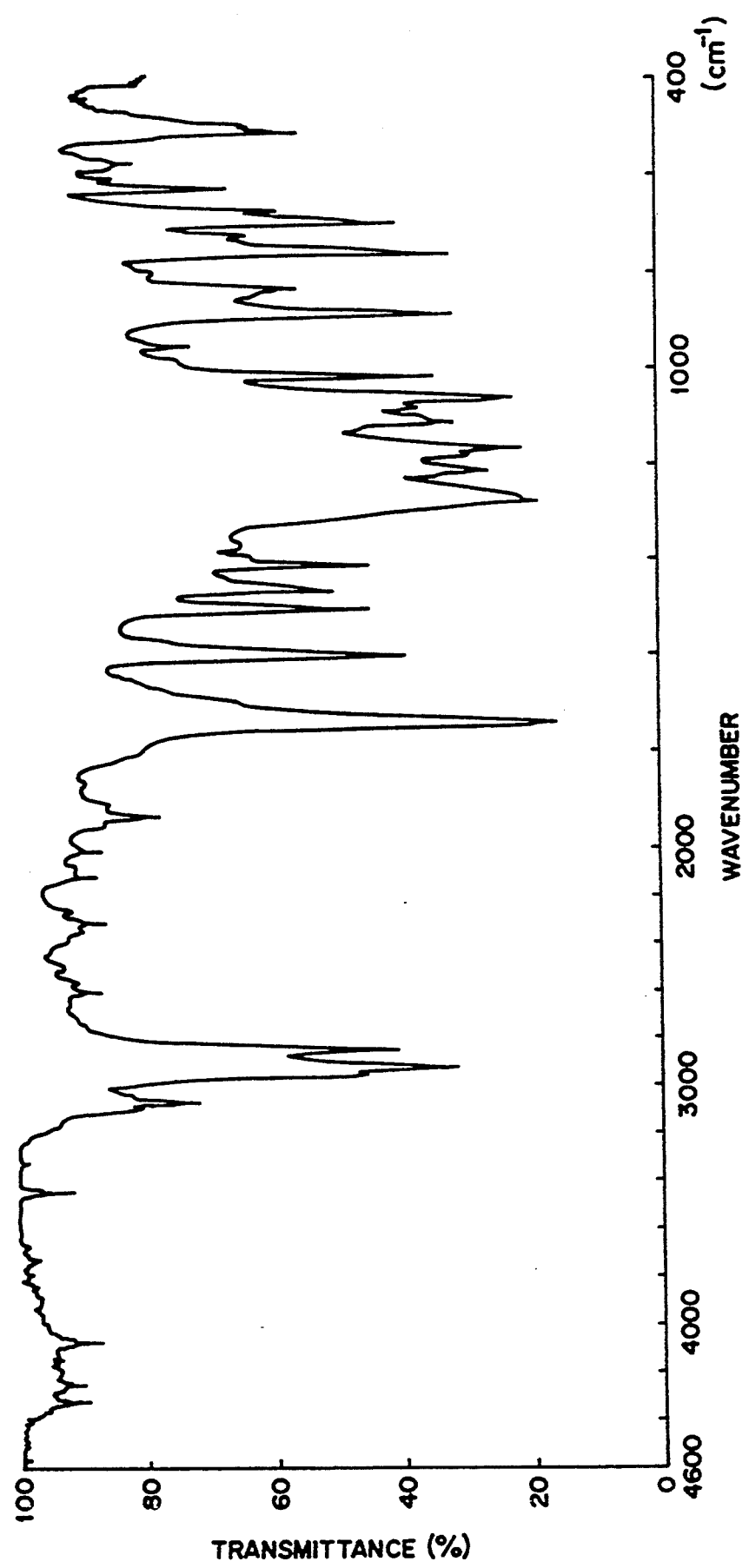
FIG. 4 shows infrared absorption spectrum of the compound of the present invention obtained in Example 6.

IR spectrum of the titled compound is shown in FIG. 4.

EXAMPLE 7

Synthesis of (S)-(−)-4-[4-(1,1,1-trifluoro-2-octyloxycarbonyl)phenyloxycarbonyl]phenyl 4-[4-(4-n-decyloxybenzoyloxy)benzoyloxy]benzoate:

chloric acid solution was added before extraction of the organic layer with methylene chloride. After the organic layer extracted was dried over anhydrous magnesium sulfate, the layer was distilled under a reduced pressure to remove the solvent until a crude product was obtained. The product was purified by silica gel column chromatography (developer: ethyl acetate/n-hexane=1/20) to obtain 1,1,1-trifluoro-2octyl S-(−)-4-benzyloxybenzoate (1.58 g, 4.00 mmol). Yield=84%.

After the benzoate compound was treated with 5% Pd on carbon (0.30 g) under a hydrogen atmosphere in ethanol (16 ml) for 10 hours, the Pd on carbon was filtered. The solvent was distilled off under reduced pressure to obtain the titled compound (1.08 g, 3.5 mmol). Yield=88%.

(2) Synthesis of 4-(1,1,1-trifluoro-2-octyloxycarbonyl)phenyl (S)-(−)-4-hydroxybenzoate:

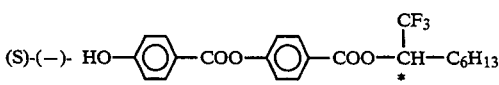

To a solution of 4-benzyloxybenzoic acid chloride (1.01 g, 4.0 mmol) in methylene chloride (10 ml) was added drop by drop at a room temeperature under a nitrogen atmosphere a solution of the compound (1.01 g, 3.5 mmol) obtained in (1) above and triethyl amine (0.41 g, 4 mmol) in methylene chloride (14 ml), followed by addition of a solution (2 ml) of N,N-dimethylaminopyridine (0.12 g, 1 mmol). After being left to

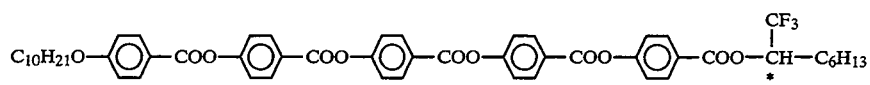

(1) Synthesis of 1,1,1-trifluoro-2-octyl (S)-(−)-4-hydroxybenzoate:

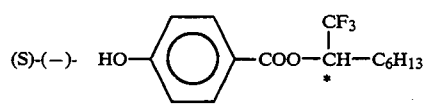

To a solution of 4-benzyloxybenzoic acid chloride (1.18 g, 4.8 mmol) in dry methylene chloride (12 ml) was added drop by drop at a room temperature under a nitrogen atmosphere a solution of (S)-(−)-1,1,1-trifluoro-2-octanol (0.81 g, 4.4 mmol) in methylene chloride. To the solution, after being stirred for 5 minutes, was added slowly and drop by drop a solution (5 ml) of triethylamine (0.47 g, 4.6 mmol) in methylene chloride, followed by addition in drop by drop of a solution (2 ml) of N,N-dimethylaminopyridine (0.16 g, 1.3 mmol) in dry methylene chloride. After the solution was left to stand at a room temperature for 2 hours, dilute hydrostand for 2 hours, dilute hydrochloric acid solution was added, before having the organic layer extracted three times with methylene chloride. After the organic layer extracted was dried over anhydrous magensium sulfate, the layer was distilled under reduced pressure to remove the solvent until a crude product was obtained. The crude product was purified by silica gel column chromatography (ethyl acetate/n-hexane=1/10) to obtain 4-(1,1,1-trifluoro-2-octyloxycarbonyl)phenyl (S)-(−)-4-benzyloxybenzoate (1.15 g, 2.23 mmol). Yield=64%.

After the benzoate compound above was treated for 10 hours in ethanol (20 ml) in the presence of 5% Pd on carbon (0.22 g), the Pd on carbon was filtered. Distillation under reduced pressure was applied to in order to remove the solvent until the titled compound (0.90 g, 2.12 mmol) was obtained. Yield=95%.

(3) Synthesis of 4-(1,1,1-trifluoro-2-octyloxycarbonyl)phenyl (S)-(−)-4-(4-hydroxybenzoyloxy) benzoate:

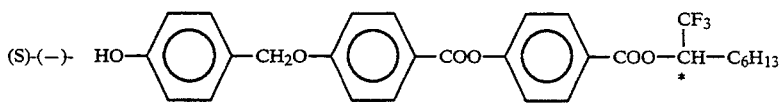

To a solution (5 ml) of 4-benzyloxybenzoic acid chloride (0.01 g, 0.4 mmol) in methylene chloride was added drop by drop at a room temperature under a nitrogen atmosphere a solution of the compound (0.14 g, 0.35 mmol) obtained in (2) above and triethylamine (0.04 g, 0.4 mmol) in methylene chloride (5 ml), followed by addition of a solution (1 ml) of N,N-dimethylaminopyridine (0.01 g, 0.1 mmol) in methylene chloride. After the solution was left to stand for 2 hours, a dilute hydrochloric acid solution was added before having the organic layer extracted with methylene chloride. After the organic layer was dried over anhydrous magnesium sulfate, the layer was distilled under reduced pressure to remove the solvent until a crude product was obtained. After the crude product was treated for 10 hours in ethanol (20 ml) under a hydrogen atmosphere in the presence of 5% Pd on carbon (0.10 g), the Pd on carbon was filtered. After the solution obtained was distilled under reduced pressure to remove the solvent, the residue was purified by silica gel column chromatography (methylene chloride) to obtain the titled compound (0.11 g, 0.2 mmol). Yield=57%.

(4) Synthesis of 4-(4-n-decyloxybenzoyloxy)benzoic acid:

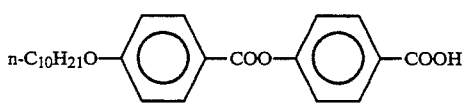

To a solution of p-hydroxybenzoic acid (0.1 g, 0.7 mmol) and triethylamine (0.07 g, 0.7 mmol) in methylene chloride (20 ml) was added p-decyloxybenzoic acid chloride (0.2 g, 0.7 mmol) and dimethylaminopyridine (0.01 g, 0.1 mmol). After the solution was stirred at a room temperature for about 20 hours, a dilute hydrochloric acid solution was added. The organic layer was extracted with methylene chloride. After the layer extracted was dried over anhydrous magnesium sulfate, the layer was distilled under a reduced pressure to remove the solvent. The residue was washed with n-hexane and dried to obtain the titled compound (0.2 g, 0.5 mmol). Yield=71%.

(5) Synthesis of 4-(4-n-decyloxybenzoyloxy)benzoic acid chloride:

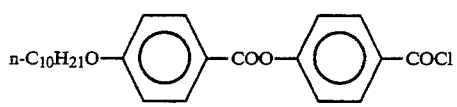

To a solution of the compound (0.2 g, 0.5 mmol) prepared in (4) above in thionyl chloride (about 10 g) was added a small amount of N,N-dimethylformamide. After the solution was heated under refluxing for 4 hours, the solution was distilled to remove unaltered thionyl chloride until the titled compound (0.29 g, 0.5 mmol) was obtained.

(6) Synthesis of 4-[4-(1,1,1-trifluoro-2-octyloxycarbonyl)phenyloxycarbonyl]phenyl (S)-(—)-4-[4-(4-n-decyloxybenzoyloxy)benzoyloxy]benzoate: (Titled compound)

To a solution of the compound (0.13 g, 0.3 mmol) obtained in (5) above in methylene chloride (10 ml) was added a solution (10 ml) of the compound (0.11 g, 0.2 mmol) obtained in (3) above, triethylamine (0.03 g, 0.3 mmol) and N,N-dimethylaminopyridine (a small amount) in methylene chloride (10 ml). After the solution was left to stand at a room temperature for 20 hours, a dilute hydrochloric acid solution was added. The organic layer was extracted with methylene chloride and then dried over anhydrous magnesium sulfate. Distillation of the layer under reduced pressure to remove the solvent gave a crude product. The product was purified by silica gel column chromatography (developer: methylene chloride) to obtain the titled compound (0.03 g, 0.03 mmol). Yield=15%.

Phase transition temperatures (°C.) which were observed under a polarizing microscpoe using a hot stage were as follows.

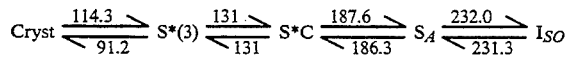

Figure 5:
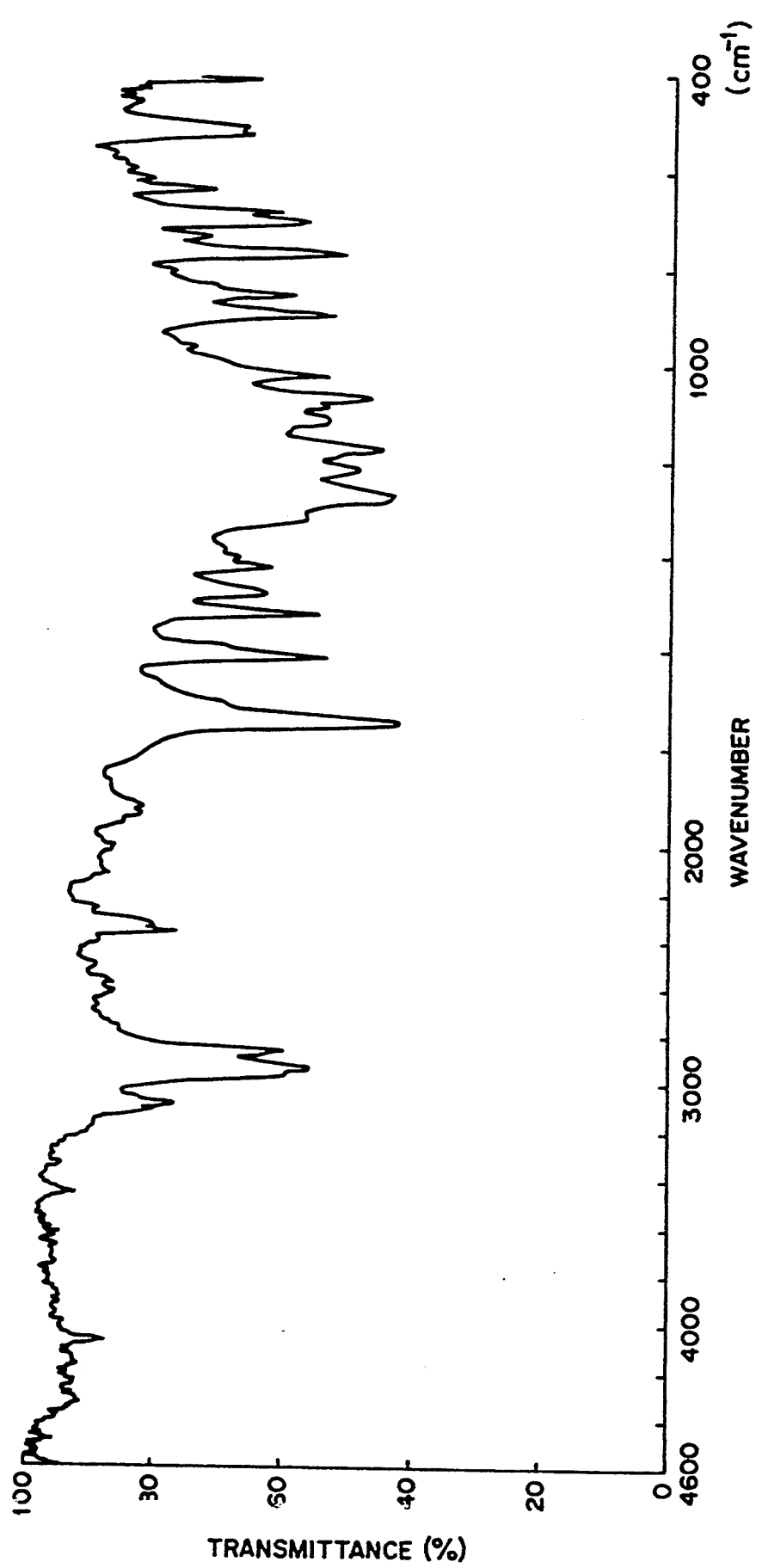
FIG. 5 shows infrared absorption spectrum of the compound of the present invention obtained in Example 7.

IR spectrum of the titled compound is shown in FIG. 5.

We claim:

1. An optically active liquid crystal compound represented by the formula (I):

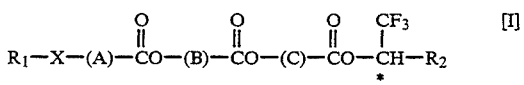

wherein $R_1$ and $R_2$ each represents a $C_4$ to $C_{18}$ alkyl group and X represents COO and (A), (B), (C) and (D) each represents

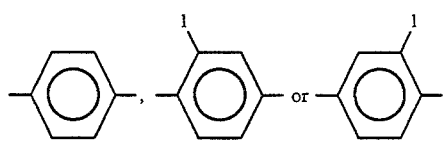

in which l represents a halogen atom.

2. An optically active liquid crystal compound represented by the formula (II):

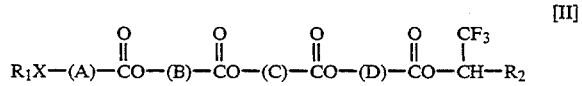

wherein $R_1$ and $R_2$ each represents a $C_4$ to $C_{18}$ alkyl group and X represents COO and (A), (B), (C) and (D) each represents

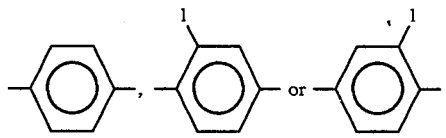

in which l represents a halogen atom.

3. An optically active liquid crystal compound which is able to exhibit tristable states, represented by the formula (IV):

$$R_1'-X'-(A)-\overset{\overset{O}{\|}}{C}O-(B)-\overset{\overset{O}{\|}}{C}O-(C)-\overset{\overset{O}{\|}}{C}O-\overset{\overset{CF_3}{|}}{\underset{*}{C}H}-R_2' \quad [IV]$$

wherein $R_1'$ and $R_2'$ each represents a straight chain $C_5$–$C_{16}$ alkyl group, and X' represents COO; and (A), (B), and (C) each represents

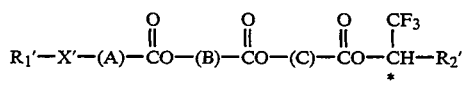

in which l represents a halogen atom.

4. An optically active liquid crystal compound which is able to exhibit tristable states, represented by the formula (V):

$$R_1'-X'-(A)-\overset{\overset{O}{\|}}{C}O-(B)-\overset{\overset{O}{\|}}{C}O-(C)-\overset{\overset{O}{\|}}{C}O-(D)-\overset{\overset{O}{\|}}{C}O-\overset{\overset{CF_3}{|}}{\underset{*}{C}H}-R_2' \quad [V]$$

wherein $R_1'$ and $R_2'$ each represents a straight chain $C_5$–$C_{16}$ alkyl group, and X' represents COO; and (A), (B), (C), and (D) each represents

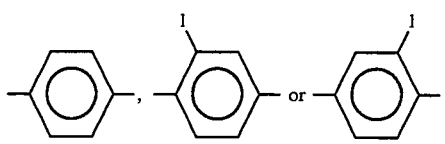

in which l represents a halogen atom.

5. An optically active liquid crystal compound represented by the formula (III):

$$R_1-X-(A)-\overset{\overset{O}{\|}}{C}O-(B)-\overset{\overset{O}{\|}}{C}O-(C)-\overset{\overset{O}{\|}}{C}O-(D)-\overset{\overset{O}{\|}}{C}O-(E)-\overset{\overset{O}{\|}}{C}O-\overset{\overset{CF_3}{|}}{\underset{*}{C}H}-R_2 \quad [III]$$

wherein $R_1$ and $R_2$ each represents a $C_4$ to $C_{18}$ alkyl group and X represents O, COO or single bond and (A), (B), (C), (D) and (E) each represents

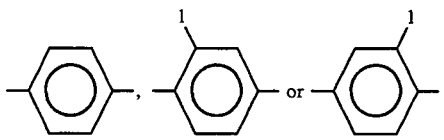

in which l represents a halogen atom.

6. An optically active liquid crystal compound which is able to exhibit tristable states, represented by the formula (VI):

$$R_1'-X'-(A)-\overset{\overset{O}{\|}}{C}O-(B)-\overset{\overset{O}{\|}}{C}O-(C)-\overset{\overset{O}{\|}}{C}O-(D)-\overset{\overset{O}{\|}}{C}O-(E)-\overset{\overset{O}{\|}}{C}O-\overset{\overset{CF_3}{|}}{\underset{*}{C}H}-R_2' \quad [VI]$$

wherein $R_1$ and $R_2$ each represents a straight chain $C_5$ to $C_{16}$ alkyl group, and X' represents O or COO; and (A), (B), (C), (D) and (E) each represents

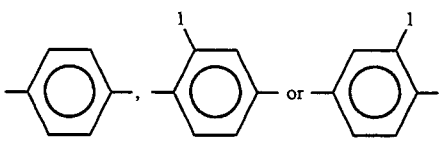

in which l represents a halogen atom.

* * * * *